United States Patent [19]

Terai et al.

[11] Patent Number: 4,966,792
[45] Date of Patent: Oct. 30, 1990

[54] METHOD OF PRODUCING GRADIENT GEL MEDIUM MEMBRANE FOR ELECTROPHORESIS

[75] Inventors: Fumitaka Terai; Kimio Yukawa; Mineo Suefuji, all of Kanagawa, Japan

[73] Assignee: Fuji Photo Film Co., Ltd., Kanagawa, Japan

[21] Appl. No.: 199,727

[22] Filed: May 27, 1988

[30] Foreign Application Priority Data

May 29, 1987 [JP] Japan ............................ 62-131504

[51] Int. Cl.$^5$ ............................................. B05D 3/12
[52] U.S. Cl. ............................. 427/358; 204/182.8; 204/299 EC; 427/420
[58] Field of Search ......... 204/182.8, 299 R, 299 EC; 252/315.1; 427/356, 358, 420; 118/410, 411; 425/131.1

[56] References Cited

U.S. PATENT DOCUMENTS

| | | | |
|---|---|---|---|
| 3,529,050 | 9/1970 | Smith | 264/174 X |
| 4,649,026 | 3/1987 | Postle et al. | 204/299 R |
| 4,657,656 | 4/1987 | Ogawa | . |
| 4,699,680 | 10/1987 | Shiraishi et al. | . |

FOREIGN PATENT DOCUMENTS

| | | |
|---|---|---|
| 0116404 | 1/1984 | European Pat. Off. . |
| 0159694 | 4/1985 | European Pat. Off. . |
| 0169397 | 6/1985 | European Pat. Off. . |
| 61-22903 | 6/1986 | Japan . |
| 61-39617 | 9/1986 | Japan . |

*Primary Examiner*—Michael Lusignan
*Attorney, Agent, or Firm*—Sughrue, Mion, Zinn, Macpeak & Seas

[57] ABSTRACT

A method for producing gradient gel medium membrane for electrophoresis for determining the base sequence of DNA or DNA partially decomposed material providing an improved productivity. High and low concentration monomer solutions are mixed with a predetermined quantity of polymerizing reaction initiator solution by a static mixer to prepare a gel forming solution for coating on a continuously moving web. The flow-rate ratio of the high and low concentration monomer solutions is gradually changed so as to vary the concentration of the monomer in the gel forming solution alternatively from low to high and from high to low along the web.

9 Claims, 3 Drawing Sheets

METHOD OF PRODUCING GRADIENT GEL MEDIUM MEMBRANE FOR ELECTROPHORESIS

BACKGROUND OF THE INVENTION

The present invention relates to a method for producing gradient gel medium membrane for electrophoresis for determining the base sequence of DNA or DNA partially decomposed material.

Conventionally, in a plane electrophoretic method, high-molecular concentration radient el of acrylamide having no self-supporting property has been obtained by forming gel in layers having concentrations different from each other and stacked on one support or between two supports in the electrophoretic direction. Such a gel has been used as a membranous material.

In the method in which gel is formed on a support, however, there has been a disadvantage in that the gel can sometimes be damaged by dropping a material other than a sample onto the gel while the gel is being formed on the support, when the gel is set in an electrophoretic tank, when the gel is in a state of preservation, or when the gel is being added with a sample to be analyzed. Therefore, close attention and a high level of skill are required in operation.

On the other hand, in a vertical electrophoretic method in which gel is formed in a mold formed by two glass plates or the like, and electrophoretic analysis is performed while holding the mold vertically, there has been a disadvantage in that it is difficult to make the mold uniform in thickness and a high level of skill is required in operation to pour a gel forming solution into a narrow mold before the gel forming solution has gelled.

Particularly, in an operation for determining the base sequence of DNA, it is desirable to form an elongated sheet of gel so that pieces of DNA, as many as possible in number, can be analyzed using one sheet of gel. However, production and handling of such an elongated sheet of gel has proved difficult. Further, since glass plates are used, there has been a disadvantage in that the glass plates are apt to break.

Recently, for the purpose of industrially producing a gradient gel material for electrophoresis, there has been disclosed a method for producing gradient gel including steps of: preparing an aqueous solution or a water dispersion liquid of a mixture of acrylic amide monomers and a cross-linking agent, adding a free radical generating material for initiating polymerization of the monomers by absorption of light irradiated on the solution, forming the solution into the shape of desired gel product, and adjusting the time period of light irradiation on the monomer solution so as to change the porosity of the gel while the solution is being irradiated so as to cause polymerization and cross-linking in the monomer solution or the monomer dispersing liquid. (See European Patent No. 0169397A).

Further, there has been disclosed a method for producing gradient gel for electrophoresis having a concentration gradient of a polymer in the electrophoresis direction and including steps of: supplying two kinds of aqueous solutions different in concentration from each other and each containing monomers, a cross-linking agent and a polymerization initiator into a forming device while mixing the aqueous solutions with a mixing ratio therebetween being changed gradually, and completing polymerization of the monomers with the cross-linking agent in the forming device. (See Japanese Patent Publications Nos. 61-022903 and 61-39617).

The former method, however has problems in that the cost is high due to the need for light irradiation equipment and generally low productivity, the resolution is low because of an increased thickness of the gel, and it is impossible to obtain gradient el having good stability and reproducibility because the reaction initiator causes polymerizing and cross-linking reactions in the presence of light even after completion of prosecution. The latter method, on the other hand, has problems in that the productivity is poor because of its batch type production system, and it is difficult to uniformly branch a medium liquid for electrophoretic separation when it is poured into forming devices, making it impossible to obtain gradient gel with good reproducibility.

To produce gradient gel medium membrane for electrophoresis with a high productivity and good reproducibility and to solve the foregoing problems, the present applicant has proposed a method for producing gradient gel medium membrane for electrophoresis including steps of: mixing high and low concentration monomer solutions supplied at respective flow rates, the ratio of which is continuously changed, with a predetermined quantity of polymerizing reaction initiator solution with a static mixer to thereby prepare a gel forming solution for use in electrophoresis, and coating a continuously moving web with the gel forming solution for electrophoresis.

In this proposed method, however, the flow-rate ratio of the high and low concentration monomer solutions is changed so that the concentration gradient changes from low to high every product unit length as shown in FIG. 3A, and therefore the distance t at the changeover length for every product unit length has been exceedingly long, that is, $t = 1.0$ m for $l = 0.4$ m.

SUMMARY OF THE INVENTION

It is therefore an object of the present invention to solve the foregoing problems and to provide a method for producing gradient gel medium membrane for electrophoresis for use in analyzing DNA sequences, in which a changeover length t for each product unit length l is made short to thereby reduce the product cost.

As a result of investigations carried out on the foregoing problems, the present inventors have found that the time taken for a rapid change in the flow rate of a pump (from a high flow rate to a low flow rate), the delay time required until completion of changeover of the coating liquid in the liquid supply system, etc., have an effect on the changeover length t. The present invention was made in light of this discovery.

Specifically, the present invention can be practiced by a method for producing gradient gel medium membrane for electrophoresis containing urea as a modifier, comprising the steps of mixing in a static mixer a predetermined quantity of polymerizing reaction initiator solution and high and low concentration monomer solutions supplied at a flow-rate ratio which is continuously changed to thereby prepare a gel forming solution for electrophoresis, and coating a continuously moving web with the gel forming solution for electrophoresis, wherein the flow-rate ratio is gradually changed so as to vary the concentration from low to high and then from high to low for adjacent product lengths along the web.

The term "static mixer" as employed herein means a mixer in which an agitating operation is performed by movement of the fluids themselves as the fluids are passed through the mixer. Examples of such a mixer include tubular mixers composed of spiral tubes, right and left tubes spiralling alternately, and propeller-shaped tubes with baffle boards.

The gel forming solution for electrophoresis according to the present invention may be any type of gel forming solution so long as it can form medium membrane for electrophoresis. Typical examples of such a gel forming solution include raw material solutions for acrylamide and agorose.

Examples of the modifier contained in the polyacrylamide gel medium membrane include compounds having at least one carbamoyl radical, specifically, urea, formamide, etc. Of those components, urea is more preferably used. The quantity of the modifier ranges from about 40 wt/V % to about 60 wt/V % calculated on the basis of the volume of aqueous gel containing monomers and a cross-linking agent. In the case where urea is employed, urea can be supplied within a range of from about 6 mols (about 360 g) to the quantity of saturated dissolution, preferably, within a range of from about 7 mols (about 420 g) to the quantity of saturated dissolution, for one liter of aqueous gel containing monomers and a cross-linking agent.

The continuously moving web according to the present invention may be formed of any suitable material having good flatness and which is nonconductive and substantially water impermeably. Polyesters such as polyethylene terephthalate, polycarbonate of bisphenol A or the like, vinyl polymers such as polymethyl methacrylate, polyethylene, polystyrene, polyvinyl chloride or the like, polyamides such as nylon or the like, or a copolymer of such materials, for example, a vinylidene chloride copolymer or a vinyl chloride copolymer, are preferably used.

The coating of the gel forming solution for electrophoresis according to the present invention may be carried out through slide bead coating, extrusion coating, hopper coating, curtain coating, or the like. The thickness of coating of the medium film is selected in accordance with the purpose of separation. Generally, the thickness should range from 50 $\mu$m to about 1.0 mm, preferably, from about 200 $\mu$m to about 0.5 mm.

The term "gradient gel medium membrane for electrophoresis" as used herein means a gel medium membrane having a concentration radient in every product unit length.

BRIEF DESCRIPTION OF THE INVENTION

DESCRIPTION OF THE PREFERRED EMBODIMENT

Preferred embodiment of the present invention will be described with reference to the accompanying drawings.

Figure 1:
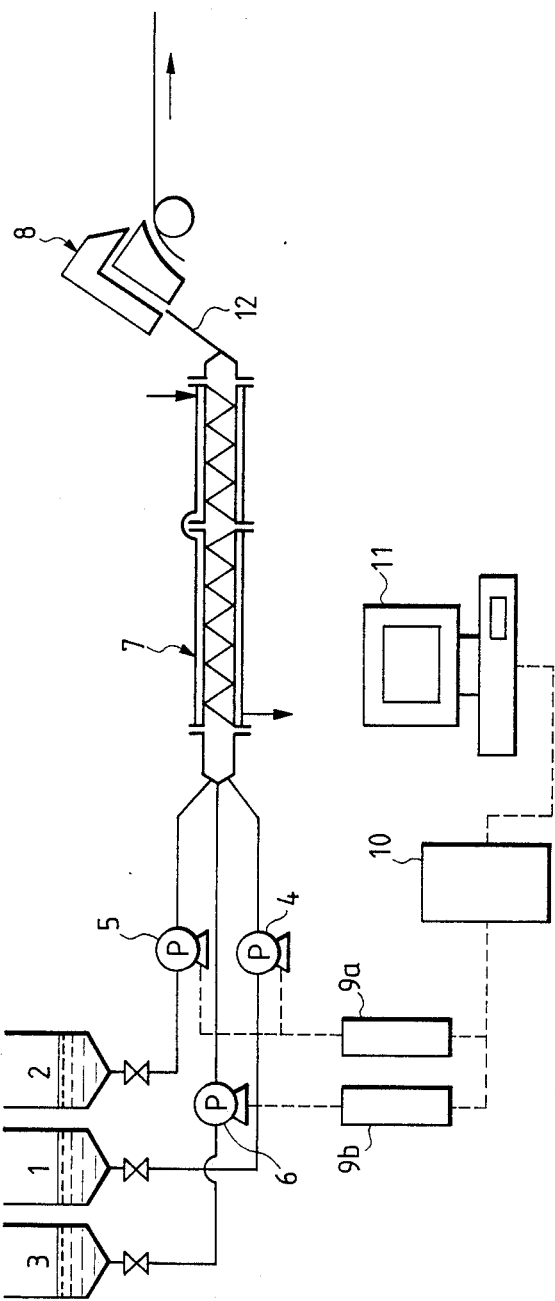
FIG. 1 is a diagram used for explaining the process of the method for producing gradient gel medium membrane for electrophoresis according to the present invention.

FIG. 1 is a diagram provided for explaining the process of a preferred embodiment of a method for producing gradient gel medium membrane for electrophoresis.

A low concentration monomer solution 1, a high concentration monomer solution 2, and a polymerizing reaction initiator solution 3 are mixed with each other while being agitated in a static mixer 7 so as to prepare a gel forming solution 12 for electrophoresis.

Figure 2A:
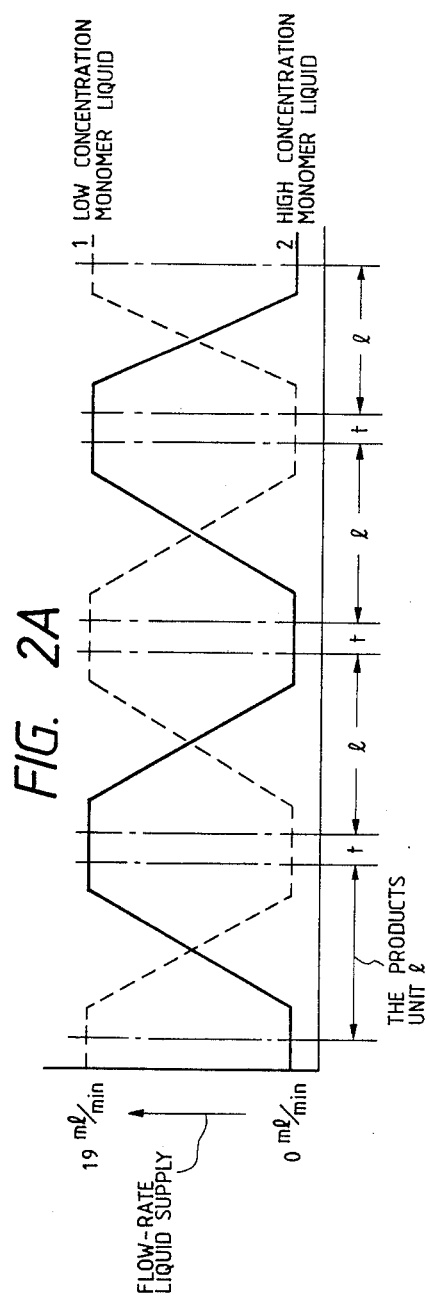
FIG. 2A is a diagram used for explaining the relation for the flow-rate ratio between two types of monomer solutions.
Figure 2B:
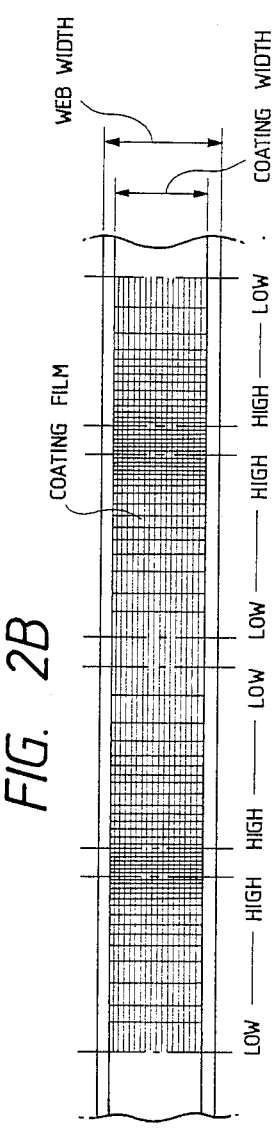
FIGS. 2B and 2C are, respectively, top and cross-sectional views of products produced according to the present invention.
Figure 2C:
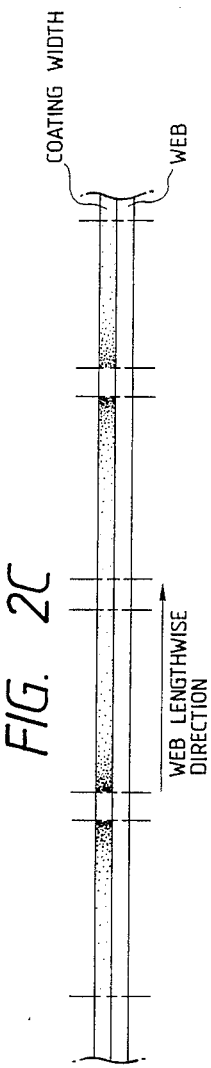

FIGS. 2A to 2C are diagrams explaining the relation of the flow-rate ratio between the high and low concentration monomer solutions according to the present invention. The continuous change of the flow-rate ratio is such that at the start the high concentration monomer solution 2 and the low concentration monomer solution 1 have flow rates of 0 ml/min and 19 ml/min respectively. Then, the respective flow rates of the high concentration monomer solution 2 and the low concentration monomer solution 1 are continuously changed in the manner shown by a solid line and a dotted line, respectively, in FIG. 2A under the condition that the sum of the flow rates is held constant at 19 ml/min. In the drawing, l represents the product unit length of the gradient gel medium membrane for electrophoresis. At the termination of each product unit length l, the respective flow rates of the high and low concentration monomer solutions 2 and 1 are 19 ml/min and 0 ml/min, and thus the medium membrane component at that point has a high concentration.

Figure 3A:
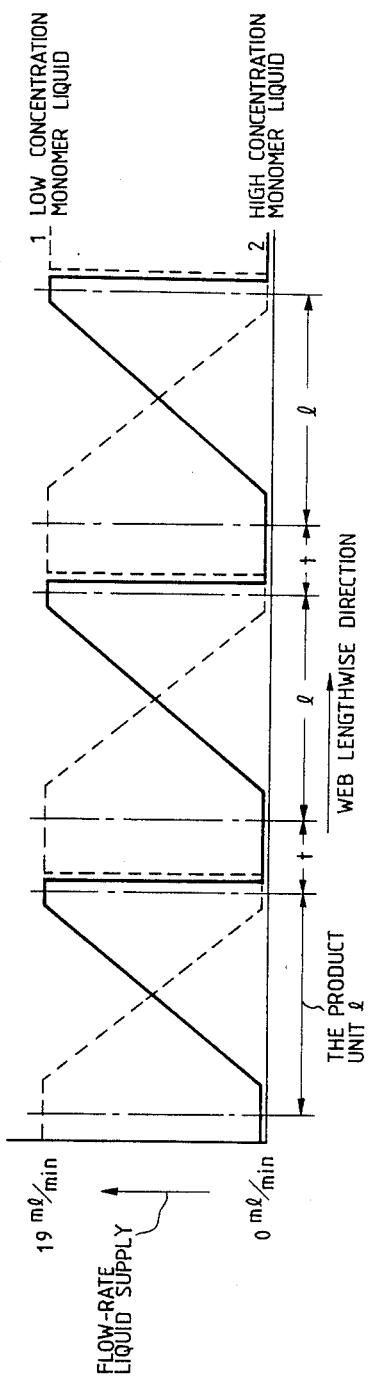
FIG. 3A is a diagram used for explaining the flow-rate ratio employed in the conventional concentration change-over process.
Figure 3B:
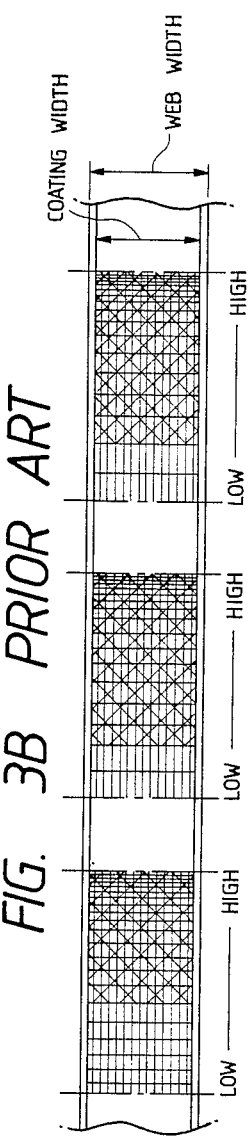
FIGS. 3B and 3C are, respectively, top and cross-sectional views of products produced according to the conventional method.
Figure 3C:
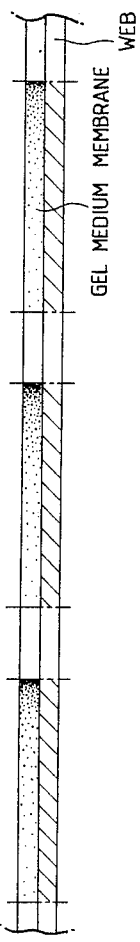

Conventionally, the flow rate of the high concentration monomer solution 2 was immediately lowered from 19 ml/min to 0 ml/min, while the flow rate of the low concentration monomer solution 1 was rapidly raised from 0 ml/min to 19 ml/min at the changeover time, as shown in FIGS. 3A to 3C. According to the present invention, however, the respective flow rates of the high and low concentration monomer solutions 2 and 1 are held as they are at the changeover time, as shown in FIG. 2A, and the next product unit length is formed with the gradient of concentration changing from high to low. Such a change of the flow-rate ratio is repeated.

In FIG. 1, flow-rate gradient liquid supply pumps 4 and 5 are controlled by a controller 9a through a computer linkage adapter 10 in accordance with instructions from a computer 11.

The polymerizing reaction initiator solution 3, on the other hand, is supplied at a predetermined rate to the static mixer 7 through a constant-flow-rate liquid-supply pump 6 controlled by a controller 9b so as to be subjected to agitation and mixing in the static mixer 7 to thereby prepare the gel forming solution 12 for electrophoresis. The gel forming solution 12 for electrophoresis is supplied to a coating head 8 so as to be applied onto a web 13.

FIG. 2B is a plan view showing the gradient gel medium membrane for electrophoresis formed according to the concentration ratio variations shown in FIG. 2A, and FIG. 2C is a cross-sectional of the same.

A changeover length t between two adjacent product unit lengths l in the drawing is punched as a sample pouring inlet portion where a sample pouring inlet is to be formed by a cover sheet or the like.

According to the present invention, by producing gradient gel medium membrane for electrophoresis containing urea as a modifier, by employing steps of mixing in a static mixer a predetermined quantity of polymerizing reaction initiator solution and high and low concentration monomer solutions supplied at a flow-rate ratio which is continuously changed to thereby prepare a gel forming solution for use for electrophoresis, and coating a continuously moving web with the gel forming solution for electrophoresis, wherein the flow-rate ratio is gradually changed so as to vary the concentration from low to high and then from high to low for adjacent product lengths along the web, it has become possible to stably produce a coating on the web with a shorter changeover time t than could be accomplished with the prior art processes because the changeover length is decreased and because the solutions can be supplied to a coating head without being mixed with each other. Further, it has become possible to improve the productivity of the process in comparison with the conventional method.

A specific example of the present invention will be described with reference to FIGS. 1 and 2A to 2C.

As the gel forming solution for electrophoresis:

Low concentration monomer solution (1) was composed of:

| Agarose | 65 g |
| --- | --- |
| Urea | 4,200 g |
| Acrylamide | 549 g |
| 1,3,5-triacryloyl-hexahydro-S-triazone | 5.7 g |
| Deionized water added up to | 9,000 ml |

High concentration monomer solution (2) was composed of:

| Agarose | 40 g |
| --- | --- |
| Urea | 4,200 g |
| Acrylamide | 1,830 g |
| 1,3,5-triacryloyl-hexahydro-S-triazine | 19 g |
| Deionized water added up to | 9,000 ml |

Buffer solution (3) was composed of:

| Tris(hydroxymethyl) aminomethane | 121.14 g |
| --- | --- |
| Boric acid | 65.4 g |
| Disodium ehtylenediamine-tetraacetate | 7.45 g |
| Deionized water added up to | 1,000 ml |

Mixed solution (4) was composed of:

| Buffer solution (3) | 750 ml |
| --- | --- |
| 2.9% polyvinyl pyrrolidone aqueous solution | 800 ml |
| 25% N,N,N,'-tetramethyl-ethylenediamine liquid | 6.7 ml |

The mixed solution (4) was added to 9,000 ml of the low concentration monomer solution (1) and to 9,000 ml of the high concentration monomer solution (2) to thereby prepare the low concentration monomer solution 1 and the high concentration monomer solution 2, respectively.

Next, as to the polymerizing reaction initiator solution 3:

Mixed solution was composed of

| 2% di-2 ethyl hexayl sulfosuccinate liquid | 100 ml |
| --- | --- |
| 0.375% riboflavin phosphonic acid ester sodium salt aqueous solution | 150 ml |
| 3.75% peroxydisulfate ammonium aqueous solution | 160 ml |

The three kinds of solutions 1, 2 and 3 were poured into respective tanks.

While keeping the sum of the respective flow rates of the low and high concentration monomer solutions 1 and 2 supplied by the flow gradient liquid supply pumps 4 and 5 at 19 ml/min, the flow-rate ratio was gradually changed so as to change the concentration ratio from low to high, and then from high to low. The polymerizing reaction initiator solution 3 was supplied to the static mixer 7 at a flow rate of 1.46 ml/min by the metering pump 6.

In the static mixer 7, the foregoing three solutions were mixed and agitated by themselves so as to prepare the electrophoretic separation gel forming solution 12.

A web 13 was coated with the gel forming solution 12 for electrophoresis by the coating head 8. During the coating process, the flow-rate ratio between the low and high concentration monomer solutions 1 and 2 was changed as shown in the FIG. 2A. The assumed concentration of the applied gel medium membrane states was as depicted in FIGS. 2B and 2C. According to the present invention, a changeover length $t=0.5$ m for every product unit length $l=0.4$ m was obtained.

As a result, productivity was raised by 50% and the production cost reduced remarkably.

Further, the gel medium membrane for electrophoresis was formed into final products through steps of attaching spacers on the opposite end portions of the web in advance, performing polymerization processing after coating, punching a comb as a sample pouring inlet, attaching a cover sheet, cutting the web into individual product lengths, etc., as disclosed, for example, in U.S. Pat. No. 4,699,680 or European Patent No. 0163472A.

According to the present invention, by producing gradient gel medium membrane for electrophoresis containing urea as a modifier by steps of mixing in a static mixer a predetermined quantity of polymerizing reaction initiator solution and high and low concentration monomer solutions supplied at a flow-rate ratio which is continuously changed to thereby prepare a gel forming solution for electrophoresis, and coating the gel forming solution for electrophoresis onto a continuously moving web, wherein the flow-rate ratio is gradually changed so as to vary the concentration from low to high and then from high to low for adjacent product lengths along the web, losses are reduced by half in comparison with the conventional method, and productivity raised by about 50%. Further, the products are improved in stability and reproducibility.

What is claimed is:

1. A method for producing a gradient gel medium membrane for electrophoresis containing urea as a modifier, comprising the steps of: mixing high and low concentration monomer solutions with a predetermined quantity of a polymerizing reaction initiator solution with a static mixer to thereby prepare a gel forming solution for electrophoresis, and coating said gel forming solution onto a continuously moving web, the flow-rate ratio of each of said high and low concentration monomer solutions being gradually changed so as to vary the concentration of monomer in said gel forming solution from low to high for a product length along said web and then from high to low for a following product length.

2. The method for producing gradient gel medium membrane of claim 1, wherein said gel forming solution comprises a material selected from the group consisting of raw material liquids for acrylamide and agarose.

3. The method for producing a gradient gel medium membrane of claim 1, wherein said web is made of a material selected from the group consisting of polyesters, vinyl polymers, polyamides, and copolymers of said materials.

4. The method for producing a gradient gel medium membrane of claim 1, wherein said step of coating comprises slide bead coating.

5. The method for producing a gradient gel medium membrane of claim 1, wherein said step of coating comprises extrusion coating.

6. The method for producing a gradient gel medium membrane of claim 1, wherein said step of coating comprises hopper coating.

7. The method for producing a gradient gel medium membrane of claim 1, wherein said step of coating comprises curtain coating.

8. The method for producing a gradient gel medium membrane of claim 1, wherein the thickness of coating of said gel forming solution on said web is in a range of 50 $\mu$m to 1.0 mm.

9. The method for producing a gradient gel medium membrane of claim 1, wherein the thickness of coating of said gel forming solution on said web is in a range of 200 $\mu$m to 0.5 mm.

* * * * *